(12) United States Patent
Fissell, IV et al.

(10) Patent No.: US 7,540,963 B2
(45) Date of Patent: *Jun. 2, 2009

(54) ULTRAFILTRATION MEMBRANE, DEVICE, BIOARTIFICIAL ORGAN, AND METHODS

(75) Inventors: William H. Fissell, IV, Ann Arbor, MI (US); H. David Humes, Ann Arbor, MI (US); Shuvo Roy, Cleveland, OH (US); Aaron Fleischman, University Heights, OH (US)

(73) Assignees: The Regents of the University of Michigan, Ann Arbor, MI (US); The Cleveland Clinic Foundation, Cleveland, OH (US)

( * ) Notice: Subject to any disclaimer, the term of this patent is extended or adjusted under 35 U.S.C. 154(b) by 360 days.

This patent is subject to a terminal disclaimer.

(21) Appl. No.: 11/437,905

(22) Filed: May 19, 2006

(65) Prior Publication Data

US 2006/0213836 A1 Sep. 28, 2006

Related U.S. Application Data

(63) Continuation of application No. 10/660,056, filed on Sep. 11, 2003, now Pat. No. 7,048,856.

(60) Provisional application No. 60/409,810, filed on Sep. 11, 2002.

(51) Int. Cl.
*B01D 71/00* (2006.01)
*C12N 5/00* (2006.01)
*A61B 5/05* (2006.01)

(52) U.S. Cl. .............. 210/645; 210/243; 210/321.72; 210/500.22

(58) Field of Classification Search ............. 210/748, 210/243, 767, 321.6, 321.72, 321.75, 321.84, 210/500.22, 645, 646, 650, 321.64; 204/415; 96/4; 600/300, 365; 435/297.1
See application file for complete search history.

(56) References Cited

U.S. PATENT DOCUMENTS

| | | | |
|---|---|---|---|
| 4,797,211 A * | 1/1989 | Ehrfeld et al. | 210/321.84 |
| 4,923,608 A | 5/1990 | Flottmann et al. | |
| 5,543,046 A * | 8/1996 | Van Rijn | 210/490 |
| 5,549,674 A | 8/1996 | Humes et al. | |
| 5,651,900 A | 7/1997 | Keller et al. | |
| 5,686,289 A | 11/1997 | Humes et al. | |
| 5,736,372 A | 4/1998 | Vacanti et al. | |

(Continued)

FOREIGN PATENT DOCUMENTS

WO 89/01967 3/1989

(Continued)

OTHER PUBLICATIONS

Park, B et al. (2002) Med Device Technol 13(2): 32-34.

(Continued)

*Primary Examiner*—Frank M Lawrence
(74) *Attorney, Agent, or Firm*—Casimir Jones SC

(57) ABSTRACT

The present invention relates to ultrafiltration. In particular, the present invention provides a compact ultrafiltration device and methods for generating an ultrafiltrate, both of which can be used for a variety of applications, including, but not limited to filtering blood, diagnostic applications, and as a bioreactor.

21 Claims, 6 Drawing Sheets

U.S. PATENT DOCUMENTS

| | | | |
|---|---|---|---|
| 5,753,014 A * | 5/1998 | Van Rijn | 96/12 |
| 5,759,830 A | 6/1998 | Vacanti et al. | |
| 5,770,076 A | 6/1998 | Chu et al. | |
| 5,770,193 A | 6/1998 | Vacanti et al. | |
| 5,770,417 A | 6/1998 | Vacanti et al. | |
| 5,776,748 A | 7/1998 | Singhvi et al. | |
| 5,798,042 A | 8/1998 | Chu et al. | |
| 5,843,741 A | 12/1998 | Wong et al. | |
| 5,882,496 A | 3/1999 | Northrup et al. | |
| 5,893,974 A | 4/1999 | Keller et al. | |
| 5,938,923 A | 8/1999 | Tu et al. | |
| 5,948,255 A * | 9/1999 | Keller et al. | 210/321.84 |
| 5,976,826 A | 11/1999 | Singhvi et al. | |
| 5,985,164 A | 11/1999 | Chu et al. | |
| 5,985,328 A | 11/1999 | Chu et al. | |
| 6,015,599 A | 1/2000 | Keller et al. | |
| 6,017,390 A | 1/2000 | Charych et al. | |
| 6,042,784 A | 3/2000 | Wamsiedler et al. | |
| 6,044,981 A | 4/2000 | Chu et al. | |
| 6,060,270 A | 5/2000 | Humes | |
| 6,107,102 A | 8/2000 | Ferrari | |
| 6,150,164 A | 11/2000 | Humes | |
| 6,180,239 B1 | 1/2001 | Whitesides et al. | |
| 6,368,838 B1 | 4/2002 | Singhvi et al. | |
| 6,368,877 B1 | 4/2002 | Zhang et al. | |
| 6,405,066 B1 * | 6/2002 | Essenpreis et al. | 600/347 |
| 6,410,320 B1 * | 6/2002 | Humes | 435/369 |
| 6,569,654 B2 | 5/2003 | Shastri et al. | |
| 6,598,750 B2 | 7/2003 | Tai et al. | |
| 7,048,856 B2 * | 5/2006 | Fissell et al. | 210/645 |

FOREIGN PATENT DOCUMENTS

| | | |
|---|---|---|
| WO | 95/13860 | 5/1995 |
| WO | 98/10267 | 3/1998 |
| WO | 98/131313 | 4/1998 |
| WO | 01/41905 | 6/2001 |

OTHER PUBLICATIONS

Voldman, J et al. (1999) Annu Rev Biomed Eng 1: 401-425.
Wagner, B (1995) Endosc Surg Allied Technol 3(4): 204-209.
Petersen, KE (1982) Proceedings of the IEEE 70:420-457.
Mrksich et al. (1996) PNAS 93:10775-10778.
Whitesides et al. z91997) Exp Cell Research: 305-313, 1997.
Mrksich, Chem. Soc. Rev., 29:267 (2000).
Desai, Med. Eng. Phys. 22:595, 2000.
Deutsch et al., J. Biomed. Mater. Res., 53:267, 2000.
Kapur et al., J. Biomed. Mater. Res., 33:205, 1996.
Brunette and Chehroudi, 121:49, 1999.
Brunette, Exp. Cell Res., 167:203, 1986.
Brunette, Exp. Cell Res. 164:11, 1986.
den Braber et al., J. Biomed. Mater. Res., 29:511, 1995.
den Braber et al., Biomaterials, 17:2037, 1996.
Curtis and Wilkinson, Biomaterials 18:1573, 1998.
Craighead et al., Biomed. Microdevices, 1:49, 1998.
Mata et al., Biomed. Microdevices 4:267, 2002.
Mata et al., J. Biomed. Mater. Res., 62:499, 2002.
Sims in Can. J. Cardiol. 7(10):431-443 (1991.
Shepro et al in FASEB J. 7:1031-1038 (1993).
Davies in Kidney International, 45:320-327 (1994).
Scott et al., J. Cell Sci. 105:269-273, 1993.
Schneider et al., Surgery 103:456-462, 1988.
Kadletz et al., J. Thoracic and Cardiovascular Surgery 104:736-742, 1 1992.
Shepard et al., Surgery 99: 318-3.about.6, 1986.
Demetriou et al., Science 23:1190-1192, 1986.
Fissell et al., J. Amer. Soc. Nephrology, vol. 13, pp. 602A, 2002.
Humes et al., Amer. J. Physiology, 271:F42, 1996.
Desai et al Adv. Drug Delivery Rev. 56:1661-1673, 2004.
Conlisk et al in Electrophoresis 24:3006-3017 (2003).
Conlisk et al in Anal. Chem 74:2139-2150 (2002).
Min Sensors and Actuators 98:368 (2004).
Desai, Tejal A., et al., "Micromachined interfaces: new approaches in cell immunoisolation and biomolecular separation," Biomolecular Engineering 17 (2000) 23-36.
European Search Report dated Feb. 17, 2009, EP Patent Application No. 03754486.3.

* cited by examiner

ULTRAFILTRATION MEMBRANE, DEVICE, BIOARTIFICIAL ORGAN, AND METHODS

The present application is a Continuation of U.S. patent application Ser.No. 10/660,056, filed Sep. 11, 2003 now U.S. Pat. No. 7,048,856, now allowed, which claims priority to U.S. Provisional Application Ser. No. 60/409,810, filed Sep. 11, 2002, both of which are herein incorporated by reference in its entirety.

The present application was funded in part with government support under grant number DK50539 from the National Institutes of Health. The government may have certain rights in this invention.

FIELD OF THE INVENTION

The present invention relates to ultrafiltration. In particular, the present invention provides a compact ultrafiltration device and methods for generating an ultrafiltrate, both of which can be used for a variety of applications, including, but not limited to filtering blood, diagnostic applications, and as a bioreactor. The present invention also provides bioartificial organs.

BACKGROUND OF THE INVENTION

Renal failure affects approximately 300,000 Americans and an unknown number of patients worldwide. Treatment methods of kidney failure currently include organ transplantation and dialysis. Organ transplantation involves a kidney from a cadaver or a living donor implanted in the anterior abdominal wall or the peritoneum of the patient with kidney failure, and the formation of vascular and urinary conduits. Alternatively, two types of dialysis are available: hemodialysis, where the patient's blood is passed against a synthetic or semisynthetic membrane and diffusive transport of toxins occurs into a bath of dialysate on the other side of the membrane, and peritoneal dialysis, wherein the patient's parietal peritoneal epithelium performs the function of the dialysis membrane. Both dialysis methods are performed at scheduled periods of time. All of these treatments are severely limited; organ transplantation is limited by a shortage of donor organs, and dialysis is limited by severe morbidity and mortality. There is evidence that the use of slow continuous ultrafiltration provides benefits when compared with the use of intermittent hemodialysis currently available. There are also components of a bioartificial kidney under development, which may replace some of the endocrine and metabolic functions of the kidney not replaced in hemodialysis.

The replacement of renal function in persons with renal failure by dialysis is dependent on the ability to filter out waste products while preserving metabolically costly proteins, peptides, and cells. In both forms of dialysis, small molecules diffuse from an area of higher concentration (blood) to an area of lower concentration (dialysate), which are separated either by a membrane of cells (the peritoneal lining) in the case of peritoneal dialysis, or a synthetic membrane in the case of hemodialysis. Transport of a molecule from one fluid to the other is proportional to the difference in concentrations of the molecule in the two fluids and is approximately inversely proportional to the molecular size, up to sizes excluded by the membrane. Thus smaller molecules are extracted from the blood more quickly than larger ones. In the native kidney, this is accomplished by a structure called the glomerulus. Blood under arterial pressure enters a the glomerular capillary, and water and small solutes are forced through a specialized tissue structure comprised of the cells and connective tissue of the glomerular capillary tuft. The cellular and molecular structure of the glomerulus imposes constraints based on molecular size and molecular charge. Molecules meeting certain size and charge constraints are dragged with the fluid and are transported at a rate directly proportional to the rate of fluid flow. For very small molecules, such as urea, clearance by either method is similar. For very large molecule, such as antibodies, the blockade to passage is similar. For molecules in between, such as β2-microglobulin, convective transport via ultrafiltration may be far more efficient than diffusive clearance through dialysis. β2-microglobulin was selected as an exemplary molecule precisely because it accumulates in renal failure and causes toxicity in the patient, and is not effectively removed by dialysis.

Present hemodialysis requires a bulky hollow-fiber dialyser that can measure over twelve inches in length and two inches in diameter, and that requires extracorporeal pumps to maintain the blood flow. Such an assembly is not suited to implantation, although wearable external devices have been tested. Furthermore, conventional hemodialysis requires a supply of purified sterile nonpyrogenic water with a balanced electrolyte composition, at flow rates of 400-800 ml/min, which is clearly unsuitable for portable or implantable use. Furthermore, the ideal permselectivity of a dialysis membrane is far from settled, with active research into the relative importance of electrostatic charge versus steric exclusion. Still further, conventional synthetic or semisynthetic membranes have a limited service life due to protein fouling and blood clotting.

Thus, what is needed is a hemofilter which more closely reproduces the filtration functions of the native kidney, both in adopting convective transport of solutes across the membrane and in requiring only modest transmembrane pressures to effect hemofiltration. It would also be useful if the filter possessed means to prevent or decrease protein fouling, resulting in an increased service life. It would also be useful if the hemofilter were compact and biocompatible.

SUMMARY OF THE INVENTION

The present invention addresses the unmet needs by providing, in some embodiments, systems and methods for filtering fluids in vivo and in vitro. In some embodiments, the present invention provides devices having membranes containing precisely configured pores that permit very controlled ultrafiltration. This provides, for example, ultrafiltration devices that function in vivo under natural in vivo pressures (e.g., systolic blood pressures). The present invention also provides devices that function in a manner that prevents protein fouling, while simultaneously being compact and biocompatible.

It is not obvious to those skilled in the art that a protein-free ultrafiltrate generated by the devices of the present invention may be in itself valuable and useful for ends other than the removal of toxins in blood filtering applications. For example, the ultrafiltration devices of the present invention also find use in diagnostic applications. For example, the devices provides a means for selectively screening out undesired molecules (e.g., proteins) within fluids, such that a particular analyte to be analyzed (e.g., small molecules such as glucose, lactic acid, electrolytes, ions, including, but not limited to, potassium, sodium, calcium, chloride, oxygen, and carbon dioxide) in the absence of interfering molecules. Present electrochemical sensors for glucose measurement are severely hampered by protein fouling of the sensor, and great effort is devoted to the invention of fouling retardants to prolong sensor life. An ultrafiltrate substantially free of proteins, but still containing smaller constituents of blood, including but not limited to sodium, potassium, chloride, glucose, provides a solution to assay for glucose concentration without protein fouling. Thus, the present invention further provides systems for use in the analysis of small molecule, including, but not limited to those listed above. Furthermore, as the intracellular aqueous mileu differs from extracellular fluid, the separate testing of whole blood and a protein and cell-free ultrafiltrate for electrolyte compositions, magnetic susceptance, optical, infrared, or magnetic resonance spectroscopy, and other physical properties of matter, provides detailed information regarding the cellular composition of the blood.

Furthermore, it is not obvious to those skilled in the art that a protein and cell free ultrafiltrate of blood so generated may be in itself valuable and useful for ends other than the removal of toxins and the measurement of the constituents of blood. The constituents of blood necessary for at least temporary support of a metabolically active cell are small in molecular size (including but not limited to oxygen, glucose, insulin, triiodothyronine, and retinoic acid, for example) while those immune mediators responsible for rejection of an allograft or xenograft are large in molecular size, such as antibodies, or components of the complement cascade, or reside in cell membranes, such as the major histocompatibility complexes. Thus a stream of ultrafiltrate of blood may be used to supply nutrients and carry away wastes by an efficient convective transport process, rather than by less efficient diffusive transport. This is directly applicable to any generalized cell population considered for transplantation, including but not limited to islet cell transplantation, liver cell transplantation, kidney cell transplantation, and in general transplant of any allo- or xeno-geneic cell type.

The ultrafiltration devices of the present invention also provide bioreactors for the growth of cells or tissues. In some such embodiments, the cells or tissues are grown with a chamber of the device such that the media in which the cells or tissues is bathed is selectively screened by the membranes of the device.

The present invention also provides bioartificial organs for in vivo or extracorporeal uses. In some embodiments, the bioartificial organs comprise cells attached to or associated with a surface. In some such embodiments, the surface is modified to control the biological activity of the attached or associated cells. In some preferred embodiments, the surface is a membrane of the present invention, having pores, as described herein. However, the present invention is not limited to the use of surfaces that comprise the membranes of the present invention.

In some embodiments, the present invention provides systems, methods and devices that utilize a defined pore shape and structure which may incorporate electrodes or other devices, chemicals, and treatments within or around a pore structure to control charge and/or size selectivity of the pore. The present invention also provides systems and methods of using such pores to produce an ultrafiltrate; in particular, such methods are used to produce an ultrafiltrate of plasma, thereby accomplishing hemofiltration and/or hemodialysis.

For example, in some embodiments, the present invention provides a membrane comprising nanofabricated pores, where each pore comprises a pore structure of defined dimensions and structure, and density. In further embodiments, at least one pore of the membrane and/or optionally at least a portion of the membrane surface comprises at least one surface treatment. Surface treatments include but are not limited to treatments that limit protein adsorption, treatments that alter or confer surface charge and surface free energy and treatments that promote adhesion of specific cell types. In other embodiments, at least one pore of the membrane comprises at least one electrode positioned on or near the membrane and/or pore such that an electric field is generated in or near the nanofabricated pore. In yet other embodiments, at least one pore of the membrane comprises any combination of a surface treatment, or any combination of a surface treatment and at least one electrode. Surface treatments and/or electric fields function to effect restriction of size and electrostatic charge of solutes that may be passed through such pores.

In other embodiments, the present invention provides an ultrafiltration system comprising: 1) a membrane comprising nanofabricated pores as described above; 2) an electrode or other device, technique, or modification to generate an electric field positioned on or near the membrane and/or pore such that an electric field is generated in or near the nanofabricated pores; 3) a housing containing the membrane and the electrode; and a fluid delivery passageway with a first end and a second end, said first end positioned outside of the housing, the second end positioned to deliver fluid across the membrane. In further embodiments, the system further comprises a membrane comprising nanofabricated pores as described, wherein the membrane also comprises a surface treatment of at least one pore and/or of the membrane, wherein the surface treatment functions to promote or retard attachment of specific cells and proteins.

In preferred embodiments, the system is configured to receive and deliver blood or plasma directly or indirectly from a subject's vasculature. In some embodiments, the housing is very small, allowing the system to be maintained on or in a subject. For example, in some preferred embodiments, the housing is made of or coated in a biocompatible material and is implanted into a subject to provide continuous hemofiltration and/or hemodialysis. In some embodiments, the system is attached to one or more additional devices that process, store, or otherwise manipulate a biological fluid and/or collect and analyze data.

In some embodiments, the system further comprises a pump configured to pass fluid through the fluid delivery passageway. In yet other embodiments, the system further comprises an actuator (e.g., a nanoscale actuator) that decreases protein fouling of the pores during fluid processing.

The present invention also provides methods of filtering a biological fluid. For example, in some embodiments, the present invention provides a method having the steps of, 1) providing a biological fluid (e.g., from a subject) and an ultrafiltration system (e.g., as described above, or elsewhere herein); 2) transferring the biological fluid into the ultrafiltration system (e.g., into the first end of the fluid passageway); 3) passing the fluid across a membrane to generated filtered fluid; and, in some embodiments, 4) transferring the filtered fluid to a subject. In some preferred embodiments, the filtered fluid that is generated is substantially free of proteins. Thus, in some embodiments, the method produces hemofiltered and/or hemodialyzed fluid.

In some preferred methods, an electric field is provided in or around at least one nanofabricated pore in the membrane. In some embodiments, the electric field is produced under conditions such that the pores provide a charge and/or size selective barrier to proteins. In some embodiments, the electric field is produced under conditions such that protein fouling is reduced in the pores.

In some embodiments, the present invention provides an ultrafiltration system comprising: a) a membrane comprising micromachined pores having a length and a width, said length being less than 500 microns (e.g., less than 200, less than 100, less than 50, less than 20, less than 10, etc. microns) and said width being less than 500 nanometers (e.g., less than 200, less than 100, less than 50, less than 20, less than 10, ... nanometers), wherein the ratio of said length to said width is at least 2:1 (e.g., 3:1, 4:1, 5:1, 8:1, 10:1, ... etc.); a housing containing said membrane; and a fluid delivery passageway with a first end and a second end, said first end positioned outside of said housing, said second end positioned to delivery fluid across said membrane. In preferred embodiments, the housing comprises a biocompatible coating that permits the system to be used in vivo. In some embodiments, the system further comprises one or more electrodes positioned on or near said membrane such that an electric field is generated in or near said pores. In some embodiments, the housing has a length and a width, said length of said housing being less than 500 millimeters (e.g., less than 400, 300, 200, 100, ... ) and said width of said housing being less than 500 millmeters (e.g., less than 400, 300, 200, 100, ... ).

The present invention further provides an ultrafiltration system comprising a membrane comprising a plurality of micromachined pores, wherein the length (the longest dimension) of each of said plurality of micromachined pores differs from the length from the other micromachined pores by no more than 30% (e.g., 20%, 10%, 5%, ... ). In some embodiments, the width (the shortest dimension) of each of the plurality of micromachined pores differs from the shortest dimension of the other micromachined pores by no more than 30% (e.g., 20%, 10%, 5%, ... ).

The present invention further provides an ultrafiltration system comprising a plurality of membranes, wherein each of the membranes comprises a plurality of micromachined pores, wherein the shortest dimension of each of the plurality of micromachined pores differs from the shortest dimension of the other micromachined pores by not more than 30% (e.g., 20%, 10%, 5%, ... ).

The present invention also provides an implantable ultrafiltration device comprising: a membrane comprising micromachined pores configured to permit ultrafiltration of blood under systolic blood pressure (e.g., without the use of a pump); a biocompatible housing containing said membrane; and a fluid delivery passageway with a first end and a second end, said first end positioned outside of said housing, said second end positioned to delivery fluid across said membrane.

The present invention further provides a diagnostic ultrafiltration device comprising a any of the above membranes; a housing containing said membrane; a fluid delivery passageway with a first end and a second end, said first end positioned outside of said housing, said second end positioned to delivery fluid across said membrane and into a chamber enclosed by said housing; and a sensor contained in said chamber, said sensor configure to detect an analyte (e.g., glucose, a pathogen, a portion of a pathogen, etc.).

The present invention also provides a bioartificial ultrafiltration device, comprising: a housing; an inlet port passing through said housing, said inlet port configured to receive a biological fluid; an outlet port passing through said housing, said outlet port configured to return a biological fluid to a subject; a membrane contained in said housing, said membrane comprising micromachined pores (e.g., any membrane disclosed herein); and a population of cells attached to said membrane. In preferred embodiments, the housing is of a size and is made of a biocompatible material to allow in vivo use. In some embodiments, the device further comprises one or more electrodes positioned on or near said membrane such that an electric field is generated in or near said pores. In some embodiments, the population of cells comprises renal proximal tubule cells. In some embodiments, a membrane prevents passage of cells or components of cells into said outlet port or into particular chambers of the device.

The present invention further provides a bioartificial ultrafiltration device, comprising: a housing; an inlet port passing through said housing, said inlet port configured to receive a biological fluid, an outlet port passing through said housing, said outlet port configured to return a biological fluid to a subject, a textured surface contained in said housing, said textured surface configured to support the attachment, growth, normal biological function (e.g., normal protein expression), or differentiation of kidney tissue; and a population of cells attached to said membrane. In some embodiments, the textured surface comprises a silicon surface (e.g., silicon or polysilicon). In some preferred embodiments, the silicon surface comprises a single-crystal silicon surface. In some embodiments, the surface is coated with extracellular matrix proteins. In some embodiments, the cells comprise renal tubule cells, pancreatic cells, hepatic cells, thyroid cells, adrenal cells, parathyroid cells, pituitary cells, hypothalamic cells, gonadal cells, prokaryotic cells, duodenal cells, other intestinal cells, gastric cells, muscle cells, fibroblast cells, and endothelial cells. In preferred embodiments, the surface is configured such that the renal tubule cells express tight junction proteins. In some preferred embodiments, the surface is prepared by generating an oxide layer, followed by deposition of a polysilicon film.

DEFINITIONS

Figure 1:
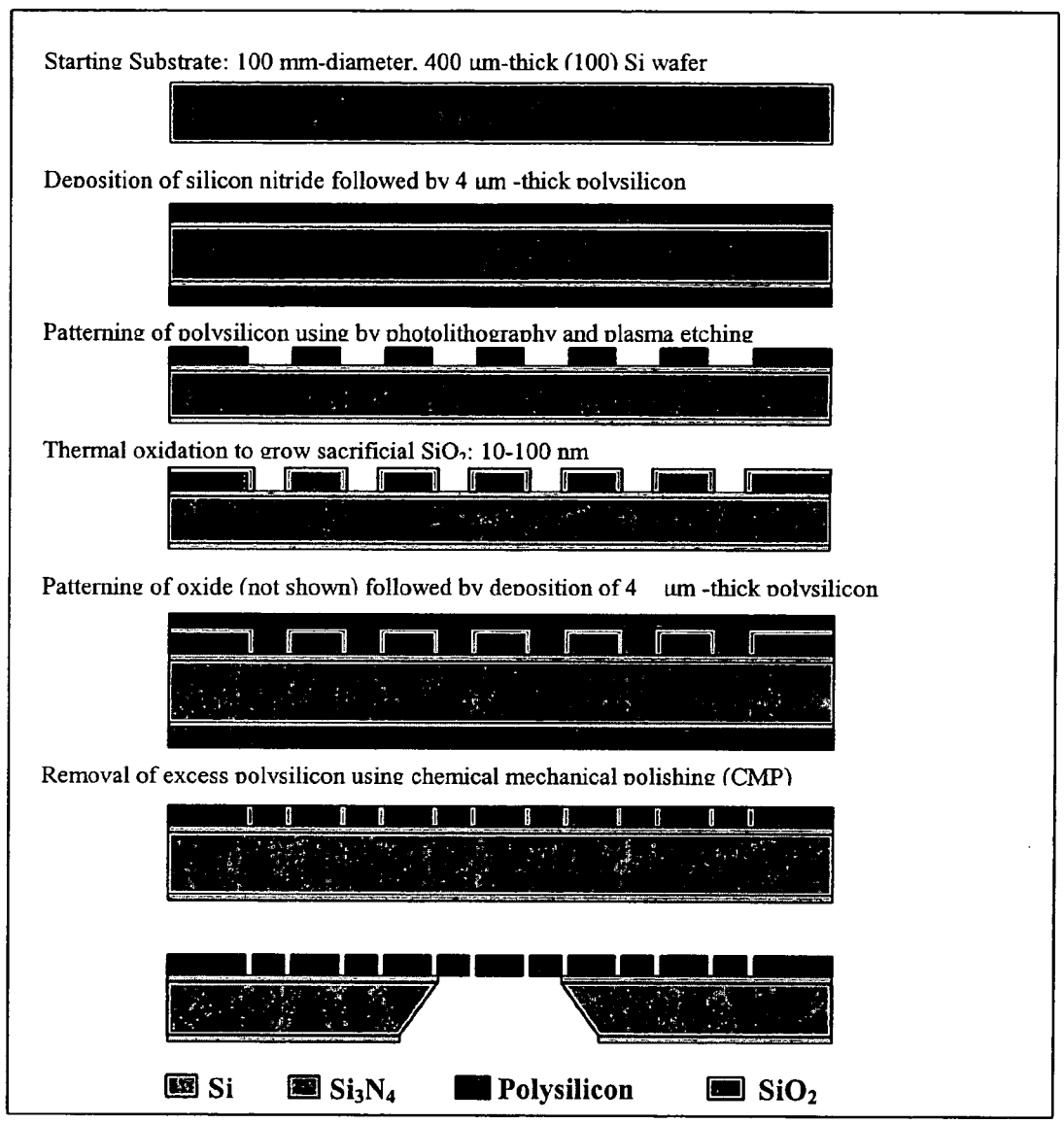
FIG. 1 shows a schematic description of process flow for the fabrication of nanomembranes showing wafer cross-sections.

To facilitate an understanding of the present invention, a number of terms and phrases as used herein are defined below:

As used herein, the term "filtration" refers to a process of separating particulate matter from a fluid, such as air or a liquid, by passing the fluid carrier through a medium that will not pass the particulates.

As used herein, the term "ultrafiltration" refers to subjecting a fluid to filtration, where the filtered material is very small; typically, the fluid comprises colloidal, dissolved solutes or very fine solid materials, and the filter is a microporous, nanoporous, or semi-permeable medium. A typical medium is a membrane. The fluid to be filtered is referred to as the "feed fluid." During ultrafiltration, the feed fluid is separated into a "permeate" or "filtrate" or "ultrafiltrate," which has been filtered through the medium, and a "retentate," which is that part of the feed fluid which did not get filtered through the medium, or which is retained by the medium.

As used herein, the term "dialysis" refers to a form of filtration, or a process of selective diffusion through a membrane; it is typically used to separate low-molecular weight solutes that diffuse through the membrane from the colloidal and high-molecular weight solutes which do not. In some embodiments, a feed of fluid is passed over a semipermeable membrane, and a feed of dialysate is passed over the other side of that membrane; the membrane is wetted by one or both solvents, and then there is diffusive transport of dissolved solutes between the fluids. The composition of one fluid, the dialysate, is used to deplete the composition of the other fluid, the feed fluid, of some molecule or molecules.

As used herein, the term "dialysate" is used to refer to the fluid into which low-molecular weight solutes diffuse through a membrane from another fluid (typically, the feed fluid) initially containing these solutes.

As used herein, the term "free of" refers to fluids of mixtures that have had one or more components (e.g., protein components) removed. "Substantially free of" fluids or mixtures are at least 50% free, preferably at least 75% free, and more preferably at least 90% free from a component with which they are otherwise naturally associated. For example, a fluid that is "substantially free of protein" is a fluid that has at least 50% or less of the protein content of an unfiltered or unpurified fluid.

As used herein, the term "microelectronics" refers to a branch of electronics that deals with the miniaturization of electronic components.

As used herein, the term "microchip" refers to another term for microsized electronic components using integrated circuit technology.

As used herein, the term "microelectromechanical systems" refers to devices that involve integrated microdevices or systems, combined with electrical and mechanical components, produced using microelectronics-compatible batch-processing techniques. These systems merge computation with sensing and actuation to perceive the physical world at a miniaturized level.

As used herein, the term "MEMS" refers to a mnemonic for microelectromechanical systems.

As used herein, the term "microfluidics" refers to MEMS devices used for the movement of fluids or gases to create microscale chemical analysis systems. This technology is becoming widely used in ink-jet printing devices for increased accuracy and resolution. It is also being investigated for its use in DNA analysis and synthesis where minute quantities of fluid are needed to assess the biochemical makeup of a cell or protein.

As used herein, the term "microfabrication" refers to a processing techniques used to manufacture microelectronics components. Typical techniques are deposition, photolithography, etching, and doping.

As used herein, the term "micromachining" refers to mechanical fabrication processes that were used to form these micromechanical parts, such as by etching areas of the silicon substrate away to leave behind the desired geometries. The development of silicon microsensors often required the fabrication of micromechanical parts (e.g., a diaphragm in the case of the pressure sensor and a suspension beam for many accelerometers). These micromechanical parts were fabricated by selectively etching areas of the silicon substrate away to leave behind the desired geometries. Hence, the term micromachining came into use in the early 1980s. Micromachining designates the mechanical fabrication processes that were used to form these micromechanical parts. The successful incorporation of techniques for the selective etching of silicon (which were initially investigated in the 1960's and 1970's), with advances in microfabrication, provided the process flexibility that was necessary to fashion micromechanical parts from silicon and related microelectronics fabrication materials.

As used herein, the term "polysilicon" refers to a polycrystalline form of silicon that is deposited as a thin film. It is used in microelectronics for transistors and wiring. In MEMS, polysilicon is usually used as structural material for devices.

As used herein the term "animal" refers to any member of the kingdom Animalia that includes living things which have cells differing from plant cells with regard to the absence of a cell wall and chlorophyll and the capacity for spontaneous movement. Preferred embodiments of the present invention are primarily directed to vertebrate (backbone or notochord) members of the animal kingdom.

As used herein, the term "subject" refers to any animal (e.g., a mammal), including, but not limited to, humans, non-human primates, rodents, and the like, which is to be the recipient of a particular diagnostic test or treatment. Typically, the terms "subject" and "patient" are used interchangeably herein in reference to a human subject.

The terms "sample" and "specimen" in the present specification and claims are used in their broadest sense. On the one hand, they are meant to include a specimen or culture. On the other hand, they are meant to include both biological and environmental samples. These terms encompasses all types of samples obtained from humans and other animals and plants, including but not limited to, body fluids such as urine, blood, fecal matter, cerebrospinal fluid (CSF), semen, and saliva, as well as solid tissue, sap, and nectar. However, these examples are not to be construed as limiting the sample types applicable to the present invention.

As used herein, the term "computer readable medium" refers to any device or system for storing and providing information (e.g., data and instructions) to a computer processor. Examples of computer readable media include, but are not limited to, DVDs, CDs, hard disk drives, magnetic tape and servers for streaming media over networks.

As used herein, the terms "processor" and "central processing unit" or "CPU" are used interchangeably and refer to a device that is able to read a program from a computer memory (e.g., ROM or other computer memory) and perform a set of steps according to the program.

DESCRIPTION OF THE INVENTION

The present invention relates to ultrafiltration. In particular, the present invention provides a compact ultrafiltration device and methods for generating an ultrafiltrate, both of which can be used for a variety of applications, including, but not limited to filtering blood, diagnostic applications, as a bioreactor, in bioartificial organs, etc. The present invention also provides a nano-machined porous structure that permits individual control of pore size and charge density.

For example, in some embodiments, the present invention provides a membrane comprising a plurality of pores, where the shapes and sizes of the pores are highly controlled. In some embodiments, the membrane further comprises at least one surface treatment. In other embodiments, the membrane further comprises at least one electric field generator, such that an electric field is produced in or around at least one pore; examples of electric field generators include but are not limited to electrodes. In yet other embodiments, the membrane further comprises at least one surface treatment and at least one electric field generator, such that an electric field is produced in or around at least one pore; examples of electric field generators include but are not limited to electrodes. In yet further embodiments, the membrane further comprises at least one of a pump and an actuator; in yet further embodiments, the membrane further comprises at least one of a surface treatment, an electric field generator, such that an electric field is produced in or around at least one pore, a pump, and an actuator.

The present invention also provides a system comprising a compartment and the porous membrane of the present invention as described above, where the porous membrane is supported within the compartment of the device, such that the presence of the membrane separates the compartment into two sub-compartments. A housing defines the outer surfaces of the compartments. A housing may be composed of any desired material. Where the system is used on or in a subject, the housing is preferably made of or coated with a biocompatible material.

Unlike the system of the prior art, the present invention provides a system that permits complete manipulation of parameters to control exclusion of molecules with particular properties (e.g., size, molecular charge, etc.). The prior art systems also do not permit exclusion of molecules within tight property parameters (e.g., sharp size, molecular charge, etc. cut-offs). Furthermore, the prior art systems do not provide ultrafiltration systems that can be used in vivo under biological pressures. Such systems would require the use of pumps to function under biological pressures, pumps that are too large for practical in vivo use.

I. Membranes

In some embodiments, the present invention provides a membrane comprising a plurality of pores, where the shapes and sizes of the pores are highly controlled. In some embodiments, the membrane further comprises at least one surface treatment. In other embodiments, the membrane further comprises at least one electric field generator, such that an electric field is produced in or around at least one pore; examples of electric field generators include but are not limited to electrodes. In yet other embodiments, the membrane further comprises at least one surface treatment and at least one electric field generator, such that an electric field is produced in or around at least one pore; examples of electric field generators include but are not limited to electrodes. In yet further embodiments, the membrane further comprises at least one of a pump and an actuator; in yet further embodiments, the membrane further comprises at least one of a surface treatment, an electric field generator, such that an electric field is produced in or around at least one pore, a pump, and an actuator.

A. Materials

The membranes of the present invention include any membrane material suitable for use in filtering biological fluids, wherein the membranes can be associated with nanofabricated pores. Examples of suitable membrane materials are known in the art and are describe herein.

In some embodiments, the membrane material is synthetic, biological, and/or biocompatible (e.g., for use outside or inside the body). Materials include, but are not limited to, silicon, which is biocompatible, coated silicon materials; thus, materials include but are not limited to, silicon, polysilicon, silicon carbide, silicon dioxide, PMMA, SU-8, and PTFE. Other possible materials include metals (for example, titanium), ceramics (for example, silica or silicon nitride), and polymers (such as polytetrafluoroethylene, polymethylmethacrylate, polystyrenes and silicones).

B. Nanofabricated Pores

A membrane of the present invention comprises at least one pore, where pore shapes include but are not limited to linear, square, circular, ovoid, elliptical, or other shapes. In some embodiments, the membrane comprises more than one pore, where the pores comprise a single shape or any combination of shapes. In some embodiments, a membrane comprises more than one pore, where the pore sizes range from about 10 to about 100 microns in any dimension; the dimensions need not be the same in any particular pore shape, the pores may comprise a single size or any combination of sizes.

In some embodiments, the sizes of the pores are highly uniform. For example, in some embodiments, the pores are micromachined such that there is less than 20% size variability, more preferably less than 10% size variability between the dimensions of the pores. In further embodiments, the sizes of the highly uniform pores are of approximate dimensions that are similar to the size of the glomerular slit diaphragm, or about 10-100 nm by 10-100 microns. In such embodiments, it is contemplated that the pores permit ultrafiltration at in vivo pressures (e.g., systolic blood pressure). Additionally, it is contemplated that such pores permit size selective exclusion of undesired molecules within specific size restrictions.

Although it is not necessary to understand the mechanism of invention in order to practice it, and although it is not intended that the invention be limited to any particular mechanism, it is contemplated that slit-shaped small pores are the preferred structure responsible for the filtration specificity of the kidney. It is further contemplated that a narrow slit retains sufficiently large solutes but provides improved hydraulic permeability when compared to a cylindrical pore.

Pressure driven ($\Delta P$) flow Q of incompressible fluid of viscosity $\mu$ through a narrow pore or pipe of rectangular cross section w×h and length L where h<<w is described by:

$$Q=(wh^3/12\ \mu L)\Delta P$$

And thus flow per unit area $Q_A$ of pore w×h is given by $$Q_A=(h^2/12\ \mu L)\Delta P$$

Pressure driven ($\Delta P$) flow Q of incompressible fluid of viscosity $\mu$ through a narrow pore or pipe of round cross section of diameter h and length L is described by $$Q=[\pi(h/2)^4/8\ \mu L]\Delta P$$

or $$Q=(\pi h^4/128\ \mu L)\Delta P$$

And thus flow per unit area $Q_A$ of a round pore of area $\pi(h/2)^2$ is given by $$Q_A=[(h/2)^2/8\ \mu L]\Delta P$$

or $$Q_A=(h^2/32\ \mu L)\Delta P$$

Thus for a given critical dimension h of a pore, a rectangular cross section pore with minimum dimension h has a higher hydraulic permeability per unit area than does a round pore of diameter h, by a factor of 2.6

Factors that determine appropriate pore size and shape include a balance between hydraulic permeability and solute permselectivity. It is contemplated that a slit shape is an optimal shape, although the present invention is not limited to slit shapes.

In preferred embodiments, the pores are created by micromachining (referred to as "nanofabrication") techniques. Micromachining is a process that includes photolithography, such as that used in the semiconductor industry, to remove material from, or to add material to, a substrate. These techniques are well known (see, for example, Park, B et al. (2002) Med Device Technol 13(2): 32-34; Voldman, J et al. (1999)

Annu Rev Biomed Eng 1: 401-425; and Wagner, B (1995) Endosc Surg Allied Technol 3(4): 204-209; Encyclopedia of Chemical Technology, Kirk-Othmer (1995), Volume 14, pp 677-709; Rierret, R F (1996) Semiconductor Device Fundamentals (Addison-Wesley); and Van Zant (1997) Microchip Fabrication $3^{rd}$. edition (McGraw-Hill); Petersen, K E (1982) Proceedings of the IEEE 70:420-457; Roy S, and Mehregany M (1999) Introduction to MEMS, in Microengineering Aerospace Systems (eds: Helvajian H; The Aerospace Press; El Segundo, Calif.) pp. 1-28, and U.S. Pat. No. 6,044,981).

Pore size distribution is controlled by variation in sacrificial layer thickness, which can be as low as 1% thermally grown $SiO_2$ across a 100 mm-diameter wafer.

C. Additional Components
1. Electric Field Generators

In preferred embodiments, the membranes have one or more electric field generators associated with them, such that an electric field is produced in or around the pores. The electric field is used, for example, to control and adjust the relative contributions of electrostatic charge and steric hindrance across a pore.

In some embodiments, an electric field is created in and around pores of a membrane by any of several means; this means include, but are not limited to, electrodes. The electrodes may be located within the pores, or on either side of the pores, or on the surface of the membrane in which the pores are fabricated.

The electrodes may be formed by well-known semiconductor processing techniques from conductive materials, such as pure metals or alloys, or other materials that are metallic conductors. Examples include but are not limited to aluminum, carbon (such as graphite), cobalt, copper, gallium, gold, indium, iridium, iron, lead, magnesium, mercury (such as amalgam), nickel, niobium, osmium, palladium platinum, rhenium, rhodium, selenium, silicon (such as highly doped polycrystalline silicon), silver, tantalum, tin, titanium, tungsten, uranium, vanadium, zinc, zirconium, platinum, palladium, iridium, or any combination or alloys of these metals; noble metals and their alloys are unreactive in biological systems. The thickness of the electrodes may range from about 10 nm to about 1 um; in some embodiments, the electrodes are about 10 nm to about 1 mm; in other embodiments, they are about 20 nm to about 100 um; in other embodiments, they are about 25 nm to about 1 um thick. Within a membrane, the electrodes may be fabricated of the same or different materials, and they may be the same size or different sizes.

Other means for generating a useful electrostatic field include but are not limited to grafting polymers, electret deposition and polarization, attachment of proteins and polymers which are negatively charged at physiologic pH (approximately 7.00-7.50).

2. Surface Treatments

In some embodiments, the membrane further comprises at least one surface treatment or modification. In some preferred embodiments, the surface treatment or modification promotes attachment of specific animal cells to the membrane, promotes attachment of desirable proteins, inhibits undesirable protein deposition on the membrane, or inhibits blood coagulation on or in the vicinity of the membrane. Such treatments or modifications may include but are not limited to patterned or unpatterned adsorption or covalent linkage to the membrane surface of RGD peptide moieties, integrins, fibronectin, laminin, collagens, or polyethylene glycol moieties. Particular cells or molecules attached to or located at the membrane surface and/or within the pores may be used to render the porous membrane more biocompatible, less thrombogenic, or may be used to alter the filtration characteristics of the pores. Furthermore, the cells may be used to process or modify the filtrate produced by the membrane. In some embodiments, modification of the pores includes but is not limited to covalent attachment of peptides or proteins, either alone or selected to promote attachment of cells such as endothelial or epithelial cells. Methods to modify silicon and silicon compounds to promote cell attachment or to retard cell attachment are well known (see, for example, Whitesides et al. (1996) PNAS 93: 10775-10778 for cell attachment; and Whitesides et al. z91997) Exp Cell Research: 305-313 for patterned attachment).

3. Pumps

Fabrication of the pores by well known MEMS techniques lends itself to the integration of such a membrane with previously realized pumps, pressure sensors, valves, etc. Thus, in some embodiments, the present invention also provides a system as described below, where the membrane and/or system further comprises microscopic peristaltic pumps, configured to direct the movement and flow of fluids. The pumps are generated by nanofabrication with "soft lithography," using techniques known in the art.

4. Actuators

The use of silicon micromachining techniques lends itself to the addition of devices to monitor or clean the membrane by thermal, acoustic, electrical or mechanical means. Thus, in some embodiments, the present invention also provides a system as described below, where the membrane and/or system further comprises actuators.

In the system of the present invention as described above, the nanoscale actuators and electronic elements incorporated during nanofabrication are utilized together to limit or reverse protein fouling of the pore, permitting prolonged or indefinite service lifetimes for a filtration device.

II. Systems

The present invention also provides a system comprising a compartment and the porous membrane of the present invention as described above, where the porous membrane is supported within the compartment of a device, such that the presence of the membrane separates the compartment into two sub-compartments. In some embodiments, the system is a device with a housing, where the housing defines the outer surfaces of the compartments. A housing may be composed of any desired material. Where the system is used on or in a subject, the housing is preferably made of or coated with a biocompatible material.

The compartment is of any appropriate shape and configuration such that the membrane within the device compartment forms two sub-compartments that are completely separate from each other, except that a first sub-compartment is in fluid connection with a second sub-compartment only by means of the pores within the membrane. In preferred embodiments, the device further comprises means for permitting entry into the first sub-compartment of a first fluid to be filtered (e.g., a feed fluid), and a means for permitting exit of excess feed fluid after filtration or of retentate, where the retentate did not get filtered through the membrane. In some embodiments, the device further comprises means for permitting exit of a second fluid from the second sub-compartment, where the second fluid is an "ultrafiltrate" or "permeate" generated from the feed fluid by means of the pores of the membrane, and optionally means for entry into the second sub-compartment of a third fluid, where such third fluid is a dialyzing fluid for the feed fluid.

Means for permitting entry of fluid into the first and second sub-compartments include but are not limited to an opening in the housing, on one side of the membrane; if such means in both sub-compartments comprise an opening, then one opening is in either side of the membrane. The opening may be of any suitable configuration, including but not limiting spheroid, elliptical, and slit-like. Means for permitting exit of fluid from the first and the second sub-compartments include but are not limited to the means for permitting entry of fluid as described above. The entry and exit means are suitably positioned in the housing to allow entry of fluid, filtration, and exit of fluid, from either or both sub-compartments. The entry and exit means may further comprise conduits for delivering fluid to the sub-compartments; such conduits include but are not limited to tubing. When present, such tubing may be inserted into the entry and or exit means, or they may be attached to the entry and/or exit means in any fashion, such as by a clamp or threaded connection, which forms a fluid-tight seal of the tubing with the entry and/or exit means.

In further embodiments, the membrane of the device of the invention as described above further comprises at least one surface treatment, as described above. In some embodiments, the surface treatment comprises attaching cells to the surface of the membrane, as described above. In these embodiments, it is contemplated the membrane is used as a scaffolding for cells to process the permeate, for example as is described in U.S. Pat. Nos. 5,549,674, 5,686,289, 6,060,270, 6,150,164, and 6,410,320, the disclosures of which are incorporated herein by reference in their entireties.

In other further embodiments, the membrane of the device of the invention as described above further comprises means for generating an electrostatic field, as described above. If desired, the device may further comprise electronic components, for example, amplifiers, filters, transmitters and/or signal preconditioning components. In some embodiments, such components can be incorporated onto the surface of the membrane. In particular, if the membrane comprises elemental silicon, well known integrated circuit technology may be used to place all the circuitry in miniaturized form on a single chip, which is incorporated into the membrane or placed onto and/or attached to the surface of the membrane.

In yet other further embodiments, the membrane of the device of the invention as described above further comprises at least one surface treatment, and at least one means for generating an electrostatic field.

III. Uses

The device of the present invention can filter any fluid from which it is desired to filter one or more types of molecules. The size, shape, array pattern, and charge across a pore are selected in accordance with the molecules to be filtered. Fluids that can be filtered include but are not limited to biological fluids, including blood and plasma. Illustrative, non-limiting uses are described below to highlight the flexibility of the present invention.

A. Hemofiltration

In some embodiments, the ultrafiltration devices of the present invention are used for hemofiltration. The kidney's functional unit, the nephron, provides for elimination of wastes and toxins without the need for specific enzymes and transporters for each toxin. All but the large proteins and cellular elements in the blood are filtered; a system of cells then reclaims specific filtered substances needed by the body, and allows all others to pass as urine. Filtration is accomplished by the glomerulus, a tuft of capillaries supported by a basement membrane and specialized epithelial cells called podocytes. The filtrate is then passed to the renal proximal tubule, a hollow tube of cells surrounded by capillaries, which accomplishes the bulk of reclamation, as well as other metabolic functions, including excretion of acid as various products.

Silicon micromachining allows the fabrication of intricate structures on a subcellular scale. The facility with which this technology permits microfluidic control, patterned deposition of cells and extracellular matrix proteins, and immunoisolation of cells lends itself to the tissue engineering of artificial organs. The engineering of nanoscale semiconductor filtration membranes permits independent control and investigation of size-charge selectivity; these processes and resulting information can then be used in tissue engineering of nephronal units.

In some embodiments, the present invention provides a membrane comprising a plurality of pores, where the shapes and sizes of the pores are highly controlled. Nanoporous membranes can be fabricated as described in Example 1. This Example describes the design and construction of polysilicon membranes with 10 to 100 nm pores. These nanoporous membranes were subsequently characterized.

The nanoporous membranes were fabricated by standard silicon bulk and surface micromachining processes. The pore structure was defined by deposition and patterning of a polysilicon film on the silicon wafer. The critical submicron pore dimension is defined by the thickness of a sacrificial $SiO_2$ layer, which can be grown with unprecedented control to within +/−1 nm. The oxide layer is etched away in the final processing step to create the porous polysilicon nanomembrane.

Membranes were mounted on polycarbonate filter inserts and examined under light microscopy for breaks or pinholes. Carriers were inserted into an Ussing chamber device fitted with pressure transducers, and both sides of the membrane were primed with aqueous solution. One side of the chamber was connected to a collection vessel at atmospheric pressure, and the other to a calibrated syringe. Syringe pumps were used to deliver fluid at set rates to the membrane, and the pressure generated by flux through the membrane was measured.

Figure 2:
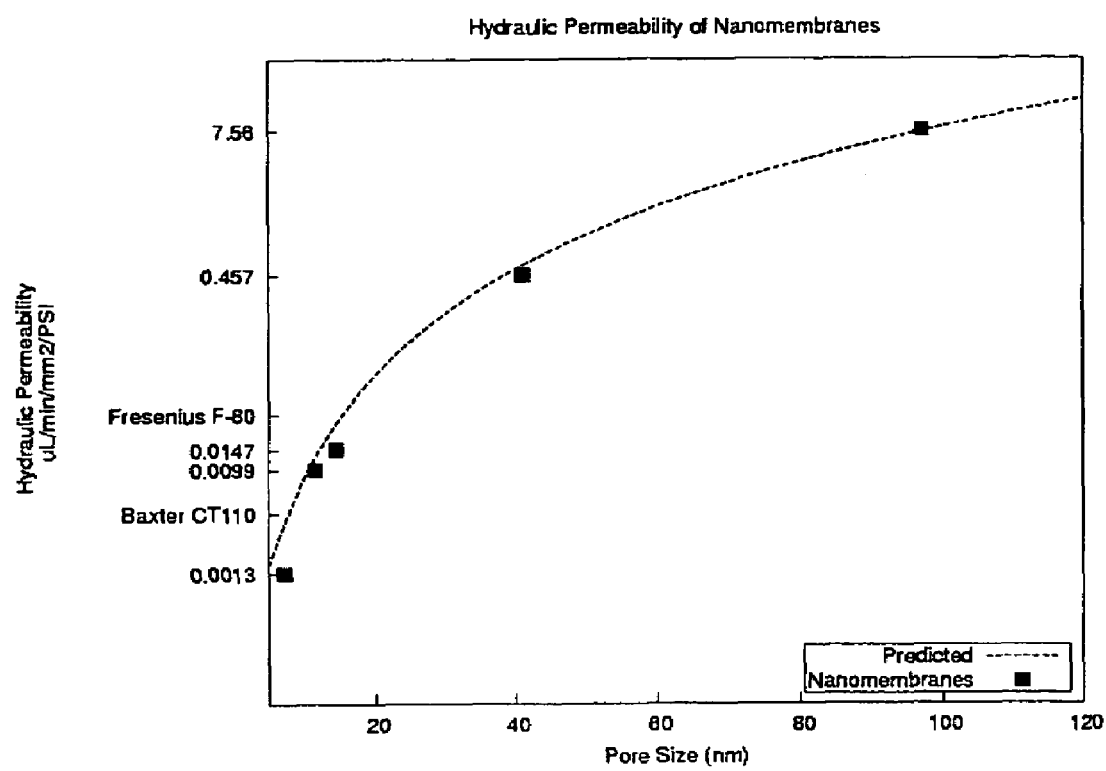
FIG. 2 shows a graph of hydraulic permeability of nanofabricated membranes of the present invention, with hydraulic permeabilites of two commercial polymer dialysis membranes (Baxter CT110 and Fresenius F-80) plotted for comparison.

Excellent agreement was obtained between the observed and predicted hydraulic resistance. The hydraulic permeability was similar to that of commercial ultrafiltration membranes, suggesting that repeatable pressure-driven hydraulic flows may be observed in micro- and nano-machined membranes (FIG. 2). These results are the first known reported results of the application of micromachining technology to the challenge of renal replacement therapy.

In other embodiments, the present invention provides a device as described above that is a compact biocompatible hemofilter that reproduces the filtration functions of the native kidney.

In these embodiments, the sizes of the membrane pores are highly uniform and of approximate dimensions which are similar to the size of the glomerular slit diaphragm; the device functions to filter the blood during hemodialysis. In further embodiments, the membrane of the device further comprises means for generating an electrostatic field. Although it is not necessary to understand the underlying mechanism to practice the invention, and the invention is not intended to be limited to any particular mechanism, it is contemplated that the electrostatic field in the pore serves to retard fouling of the membrane and/or membrane pores, to effect permselectivity of the membrane pores, or possibly to alter hydraulic permeability of the membrane pores. Compounds that foul a membrane and/or membrane pores include but are not limited to proteins, nucleic acids, lipids, polysaccharides, viruses, bacteria, and cellular debris. In other embodiments, it is further contemplated that the electrostatic field generates or controls electroosmotic flow. In these embodiments, the electrostatic field is used to draw fluid from one side of a pore to another.

This approach, termed electroosmotic pumping, is the bulk movement of liquid and is dependent on the surface charge of the pore wall as well as the ions in the solution.

In operation, blood is directed from a patient's vasculature, in either an extra- or intra-corporeal circuit, into the first sub-compartment of the device. After the blood is filtered, it exits the first sub-compartment, and is returned to/is directed back into patient's vasculature. The route of the blood from the patient through the device and back into the patient is referred to as the "blood flow." In some of these embodiments, the blood flow may be assisted or directed by pumps. In some of these embodiments, an ultrafiltrate free of proteins is formed by hydrostatic pressure of blood against the membrane. In some of these embodiments, the ultrafiltrate fills the second sub-compartment during filtration, and then exits the sub-compartment. In some embodiments, the exit means for the ultrafiltrate include but are not limited to extraction and draining, where draining may be either by active or passive means. In yet additional embodiments, the ultrafiltrate may be channeled to further devices, which include but are not limited to testing devices and bioreactors, or it may be removed for disposal. Removal may be either intracorporeally, as for example by diversion to the bladder, ileal pouch, or other anatomic conduit, or extracorporeally, as to an external pouch.

In some of these embodiments, the membrane pores, and/or either or both surfaces of the membrane itself, are kept free of debris by electrostatic or electromechanical devices as described above. The membrane is kept free of debris either by preventing the debris from accumulating on the surface, as for example by maintenance of a steady electrical current, or by removing accumulated debris, as for example by administering intermittent electrical current or pulses of current.

By means of the device of the present invention as described above, the device mimics the native filtration function of the kidney by producing an ultrafiltrate of plasma similar to that produced by a kidney. Moreover, the ability to prevent fouling of the membrane results in a long service life from the membrane, such that the membrane can be incorporated within a permanent implantable artificial kidney.

Other filtration applications to which it may be suited are also contemplated.

B. Diagnostic Uses

The ultrafiltration devices of the present invention also find use in diagnostic applications. For example, the devices provides a means for selectively screening out undesired molecules (e.g., proteins) within fluids, such that a particular analyte to be analyzed (e.g., small molecules such as glucose, electrolytes, ions, etc.) in the absence of interfering molecules. For example, present electrochemical sensors for glucose measurement are severely hampered by protein fouling of the sensor, and great effort is devoted to the invention of fouling retardants to prolong sensor life. An ultrafiltrate substantially free of proteins, but still containing smaller constituents of blood, including but not limited to sodium, potassium, chloride, glucose, provides a solution to assay for glucose concentration without protein fouling.

The device may be used to detect any desired analyte. In some embodiments, the analyte is a small molecule. In other embodiments, the analyte is a pathogen or a molecule or molecular complex associated with the presence of a pathogen in a sample (e.g., in a blood sample).

In some embodiments, the diagnostic devices are applied on or in a subject for monitoring the presence of or amount of an analyte of interest. For example, a glucose or electrolyte sensor monitors (e.g., at one or more time points or continuously) blood analyte levels. A processor associated with the device reports this information to the subject or to the appropriate medical personnel (e.g., by displaying the analyte concentration or by transmitting the analyte concentration—e.g., to a computer, PDA, phone, or other device). In some embodiments, the processor triggers, where appropriate, release of a drug or other substance (e.g., insulin) based on the measured concentration so as to alter the physiology of the subject appropriately. In some embodiments, changes in analyte concentration are measured in response to changes in the environment (e.g., ambient environment, diet, etc) or upon administration of test compounds (e.g., drugs) to the subject (e.g., for testing the safety or efficacy of drugs).

In other preferred embodiments, the device is associated with another medical device (e.g., a catheter) that is used for in vitro or in vivo detection of the desired analyte. The sensors of the present invention, provide over existing sensor technology (e.g., U.S. Pat. No. 6,405,066, herein incorporated by reference in its entirety).

C. Bioreactors

In some embodiments, the system is used as a convectively fed bioreactor for cell growth and tissue engineering, for example, as described in U.S. Pat. No. 7,332,330 the contents of which are herein incorporated by reference in their entirety. In some such embodiments, cells or tissues are applied to a surface (e.g., a membrane, a chamber surface) or are maintained in suspension in a chamber, such that one or more desired fluid flows from the system are exposed to the cells (e.g., exposure of filtered or unfiltered biological fluids to the cells). In some embodiments, the system is configured to permit the exposure of synthetic growth media (e.g., with or without serum) to the cells, alone, or in combination with filtered or unfiltered biological fluid. In some embodiments, the cells are transgenic cells. In some embodiments, the system is used as a screening system to select cells, genes, drugs, proteins, and/or growth conditions with desired characteristics and properties.

The cells or tissues may also be used to express or provide one or more desired factors to a filtered biological fluid that is to be returned to a subject or otherwise manipulated or analyzed.

IV. Bioartificial Organs

The present invention also provides bioartificial organs for in vivo or extracorporeal uses. In some embodiments, the bioartificial organs comprise cells attached to or associated with a surface of a device. In some such embodiments, the surface is modified to control the biological activity of the attached or associated cells. In some preferred embodiments, the surface is a membrane of the present invention, having pores, as described herein. However, the present invention is not limited to the use of surfaces that comprise the membranes of the present invention. In preferred embodiments, the devices are configured to combine hemofiltration with cell therapy in a manner that mimics or supplements the function of a healthy organ.

In some embodiments, the cells of the bioartificial organ are supplied with nutrients by an ultrafiltrate stream generated by ultrafiltration of blood or body fluids by a membrane of the present invention. In other embodiments the cells and tissues of the bioartificial organ are grown on or attached to a membrane of the present invention. In other embodiments the cells and tissues of the bioartificial organ are grown on or attached to a membrane of the present invention and the cells of the bioartificial organ are supplied with nutrients by an ultrafiltrate stream generated by ultrafiltration of blood or body fluids by a second membrane of the present invention.

In preferred embodiments, the bioartificial organ is a bioartificial kidney. Such devices, find use, for example, in the treatment of end-stage renal disease. The compact nature of the devices of the present invention allows for in vivo or easy, portable, extracorporeal treatment. In-center dialysis, the most common mode of treatment of end-stage renal disease, is expensive and labor-intensive. Thus, the miniature devices of the present invention simplify, improve, or relocate to home or in vivo, the treatment of end-stage renal disease, resulting in cost savings and improved quality of life for treated subjects. Thus, the present invention provides advantages over or extensions to existing bioartifical kidneys (see e.g., U.S. Pat. No. 6,150,164, herein incorporated by reference in its entirety).

A. Surfaces

In some embodiments, the devices comprise a surface for the growth of cells (see e.g., section III, C above describing bioreactors). The present invention is not limited by the nature of the surface on which the cells are grown. Any surface that permits cell to have desired biological properties (e.g., attachment, growth, cell division, protein production, protein secretion, membrane fluidity, endocytosis, etc.) is contemplated by the present invention. The material properties upon which cells are grown influence cell attachment and differentiation. This includes geometric patterning and distribution of ECM binding proteins, surface topology, and porosity of the surface. In some embodiments, the surfaces are coated with self-assembling monolayers, multilayers, or particles. A wide variety of patterned self-assembling materials are known (see e.g., Mrksich, Chem. Soc. Rev., 29:267 (2000) and U.S. Pat. No. 6,017,390). The coating used on the surfaces can comprise or provide and attachment site for ligands for selective protein/cell attachment or rejection, or otherwise selectively attract or reject desired or undesired molecules or materials.

Examples of surface modification that allow one to tailor the properties of the associated cells are described in Examples 4 and 5 and are found in Desai, Med. Eng. Phys. 22:595, 2000, Deutsch et al., J. Biomed. Mater. Res., 53:267, 2000, Kapur et al., J. Biomed. Mater. Res., 33:205, 1996, Brunette and Chehroudi, 121:49, 1999, Brunette, Exp. Cell Res., 167:203, 1986, Brunette, Exp. Cell Res. 164:11, 1986, den Braber et al., J. Biomed. Mater. Res., 29:511, 1995, den Braber et al., J. Biomed. Mater. Res., 17:2037, 1996, Curtis and Wilkinson, Biomaterials 18:1573, 1998, Craighead et al., Biomed. Microdevices, 1:49, 1998, Mata et al., Biomed. Microdevices 4:267, 2002, Mata et al., J. Biomed. Mater. Res., 62:499, 2002, and U.S. Pat. Nos. 5,776,748, 5,843,741, 5,976,826, 6,569,654, 5,770,193, 5,759,830, 5,736,372, and 5,770,417, each of which is herein incorporated by reference in their entireties.

In some preferred embodiments, the surface is a membrane of the present invention (see e.g., section I, above). Use of such membranes provides a number of advantages, including the ability to miniaturize the bioartificial device to allow in vivo use or efficient and convenient extracorporeal use. An example of a nanoporous membrane for use in the bioartificial organs of the present invention is described in Examples 4 and 5.

The surface of may be precoated with suitable extracellular matrix (ECM) components including Type I collagen, Type IV collagen, laminin, Matrigel, proteoglycan (such as heparin sulfate and dermatan sulfate) fibronectin, and combinations thereof to form an ECM layer. Once an ECM layer has been established on the surface, this layer is then seeded with desired cells.

B. Cells

A variety of cells find use in the bioartifical organs of the present invention. In some embodiments the cells of the bioartificial organ are liver, duodenal, intestinal, gastric, pancreatic, thyroid, parathyroid, adrenal, gonadal, pituitary, or hypothalamic cells. In some embodiments the cells of the artificial organ are bone marrow cells. In other embodiments the cells of the bioartificial organ are stem cells, feeder cells, or other precursor cells. In still other embodiments, the cells of the bioartificial organ are derived from stem or precursor cells. In still other embodiments, the bioartifical organ comprises cells that induce the differentiation of nearby cells or attract nearby cells to the organ. In some embodiments, the cells comprise one or more transgenes (e.g., having inducible promoters).

In preferred embodiments, the cells are from kidney or associated tissue. Cells from many segments of the nephron have been grown in primary culture (see for example, Handler & Burg in "Application of tissue culture techniques to study of renal tubular epithelia" in Windhager & Giebisch (eds): Handbook of Physiology, Section 8, Renal Physiology, American Physiological Society, Williams & Wilkins, Baltimore). Specific cells have been separated on the basis of differential growth, by mechanical dissection, by differential centrifugation and with the aid of specific antibodies (immunodissection).

In some preferred embodiments, the cells are renal proximal tubule cells. These cells replace the metabolic, endocrine, and immunologic functions of a damaged kidney. Cells are grown on the appropriate surface and then exposed to ultrafiltrate. The cell-exposed ultrafiltrate is then returned to a subject. It is contemplated that the cell-exposed ultrafiltrate contains serum appropriate levels of desired biological components (e.g., 1,25 dihydroxy-vitamin $D_3$, sodium, glucose, etc.).

In some embodiments, a mixture of cell types is associated with the surface. In some such embodiments, a first layer of a first cell type is grown, which provides a new surface for the growth a second or additional cell types. For example, pericyte, vascular smooth muscle or mesangial cells can be first seeded on a ECM layer and allowed to reach confluence. Thereafter, endothelial or other cells can be seeded. Pericyte cells are described by Sims in Can. J. Cardiol. 7(10):431-443 (1991) and Shepro et al in FASEB J. 7:1031-1038 (1993), incorporated herein by reference. Mesangial cells, the preferred type of pericyte cell, are described by Davies in Kidney International, 45:320-327 (1994), incorporated herein by reference.

Suitable culturing techniques useful for seeding these cells on the surface are described by Scott et al., J. Cell Sci. 105: 269-273, 1993; Schneider et al., Surgery 103:456-462, 1988; Kadletz et al., J. Thoracic and Cardiovascular Surgery 104: 736-742,1 1992; Shepard et al., Surgery 99: 318-3.about.6, 1986; and Demetriou et al., Science 23:1190-1192, 1986.

EXAMPLES

The following examples are provided in order to demonstrate and further illustrate certain preferred embodiments and aspects of the present invention and are not to be construed as limiting the scope thereof Example 1

Nanofabrication of Membranes

This example describes the process flow for fabrication of nanomembranes; this process is depicted in FIG. 1. The starting substrate is a 400 µm-thick, 100 mm-diameter, double side polished (100)-oriented silicon wafer that is obtained from a commercial vendor of semiconductor substrates. The wafer is coated with a 5000 Å-thick layer of low-stress silicon nitride (LSN) by low-pressure chemical vapor deposition (LPCVD). Next, a 4 μm-thick film of polysilicon is deposited by LPCVD (FIG. 1) and followed by thermal oxidation to grow a 2500Å-thick layer of $SiO_2$. The oxide layer on the wafer front side is then patterned by photolithography and wet etching in buffered hydrofluoric acid (BHF) to create an etch mask, which is used to pattern the underlying polysilicon film by reactive ion etching (RIE) in chlorine plasma. Afterwards, BHF is used to remove the masking oxide on both wafer front and back sides and followed by RIE to remove polysilicon on the wafer back side (FIG. 1). Next, thermal oxidation is performed to realize a 20nm-thick $SiO_2$ film that will define the pore size in the nanomembrane (FIG. 1). It should be noted that other pore sizes, if desired, could be realized by varying the thickness of the $SiO_2$. The anchor regions are then defined by selectively patterning the oxide on the wafer frontside using photolithography and BHF. Next, another 4mm-thick polysilicon film is deposited by LPCVD (FIG. 1) and followed by global planarization by chemical-mechanical polishing (CMP) to remove any excess polysilicon and expose the pore regions on the frontside (FIG. 1). The polysilicon and LSN on the backside are then removed by RIE in chlorine and SF6 plasma, respectively, and followed by a LPCVD deposition of LSN on both front and back sides of the wafer (FIG. 1). Afterwards, the LSN on the wafer backside is patterned using photolithography and RIE to define an etch mask (Fig. 1) for the subsequent KOH etch to create suspended membranes (FIG. 1). Finally, the masking LSN and $SiO_2$ films are etched in concentrated hydrofluoric acid to realize the nanomembranes (FIG. 1).

Example 2

Extracorporeal Hemofiltration

Figure 3:
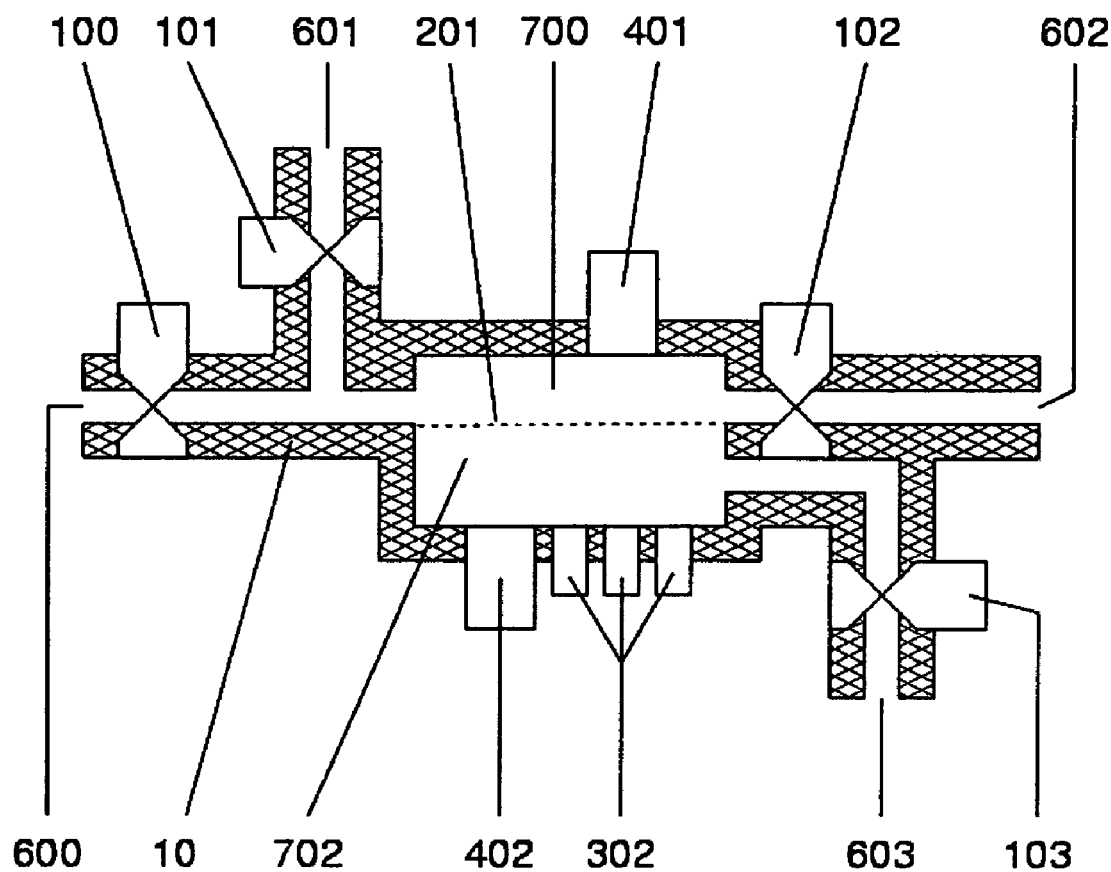
FIG. 3 shows an extracoproeal hemofiltration device in some embodiments of the present invention.

This example demonstrates how a nanofabricated nanoporous membrane may be used to form an extracorporeal hemofiltration device (see e.g., FIG. 3). Blood from a patient or from a stored supply is directed to an orifice 600 by means of a cannula, catheter or other means. An optional pump 100, which may be peristaltic, rotary, roller, or other, is used to regulate a flow of blood to a chamber 700, which contains a pressure sensor 401 and is bounded by a membrane 201 composed of a plurality of pores. Said pores may be shaped to optimize hydraulic permeability, and may be all alike or dissimilar. Furthermore, said pores may contain or comprise electrodes, surface treatments, or be coated with chemicals, polymers, proteins, sugars, and the like to impart a particular electrostatic charge to the pore or a region around the pore, and impart an electric field within the pore. Blood exits the chamber 701 via an orifice 602 with an optional pump 102 which may be peristaltic, rotary, roller, or other, and is returned to the patient or to a reservoir via cannula, catheter or other means. Fluids, in this example an electrolyte solution, or optionally an anticoagulant solution, or other solution not specified may be introduced into the blood in chamber 701 via orifice or inlet 602 and optional pump or valve 101. The pressure sensor 401, in combination with external or integrated electronics and controls, with valves and pumps 100, 101, and 102 may be used to regulate flow of blood into and out of chamber 701, and specifically to regulate and adjust the hydrostatic pressure in chamber 701. A second chamber 702 is positioned to receive filtrate passing through the membrane 201 either under force of hydrostatic pressure or eletroosmotic flow or other means not specified. Chamber 702 incorporates a second pressure sensor 402, a sensor or array of sensors 302 incorporating but not limited to optical, conductance, impedance, magnetic resonance, electrochemical, or immunologic principles, and a conduit 603 and pump or valve 103 for removal of fluid to a reservoir or drain. The sensor or array of sensors 302 may be used to monitor the composition of the ultrafiltrate and actuate alarms, valves, or other devices, including but not limited to telemetry and telephony devices, in event that a parameter measured of the ultrafiltrate falls out of a prescribed range. In this fashion a nanofabricated nanoporous membrane may be used to accomplish hemofiltration of blood.

Example 3

Continuous Blood Glucose Sensor

Figure 4:
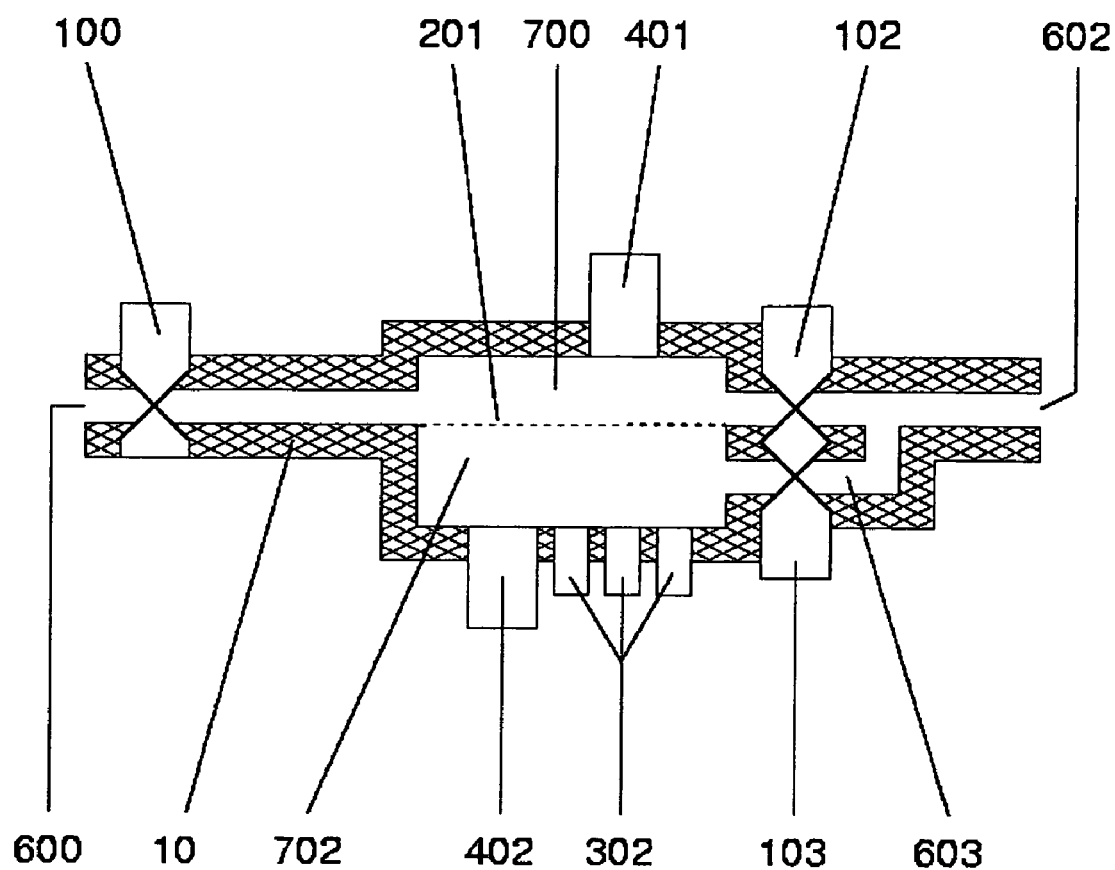
FIG. 4 shows a continuous analyte sensor in some embodiments of the present invention.

This example demonstrates how a membrane may be used to form a continuous blood glucose sensor. The novelty and advantage of this approach is the rapidity with which the glucose level in the blood is transmitted to the sensor, as glucose is carried by convection to the sensor, rather than by diffusion towards the sensor, while still affording the sensor protection from elements in the blood that may be injurious to or degrade the sensor. The example of a blood glucose sensor is not to be construed as limiting the application; it may be applied to the analysis of cell and/or protein free fluids for arbitrary analytes by arbitrary means. A preferred embodiment is illustrated in FIG. 4. Blood from the patient is directed by means of a cannula, a vascular anastamosis, a synthetic graft, or other means to an inlet 600 optionally equipped with a pump or valve or other flow controller 100 to a chamber 700, which optionally contains a pressure sensor 401 and is bounded by a membrane 201 composed of a plurality of pores. Said pores may be shaped to optimize hydraulic permeability, and may be all alike or dissimilar. Furthermore, said pores may contain or comprise electrodes, surface treatments, or be coated with chemicals, polymers, proteins, sugars to impart a particular electrostatic charge to the pore or a region around the pore, and impart an electric field within the pore. A second cannula or vascular anastamosis, or synthetic graft or other means returns blood from the chamber via an optional flow controlling device 102 and outlet 602 to the patient's blood stream. The pressure sensor 401, in combination external or integrated electronics and controls, with valves and pumps 100 and 102 may be used to regulate flow of blood into and out of chamber 700, and specifically to regulate and adjust the hydrostatic pressure in chamber 700. A second chamber 702 is positioned to receive filtrate passing through the membrane 201, and optionally incorporates a second pressure sensor 401, and a sensor or array of sensors 302 incorporating but not limited to optical, conductance, impedance, magnetic resonance, electrochemical, or immunologic principles. In the present Example, at least one of the sensors 302 is able to measure the concentration of glucose in the ultrafiltrate. The ultrafiltrate then exits the second chamber, either under hydrostatic pressure or by means of an active pump or valve 103 and is directed to an outlet 603 which joins with and is continuous with outlet 602 returning blood from the first chamber 700 to the patient's blood stream by means of a cannula or vascular anastamosis, or synthetic graft or other means. The sensor or array of sensors 302 may be used to monitor the composition of the ultrafiltrate and actuate alarms, valves, or other devices, including but not limited to telemetry and telephony devices, in event that a parameter measured of the ultrafiltrate falls out of a prescribed range. In the present example, the sensor would be connected to central processing unit incorporating a digital-to-analog converter and a means, such as an antenna or a light emitting device (LED) for transmitting the value measured by the sensor through the patients skin by electromagnetic or optical means, for detection, recording, and analysis by the patient or others. In this way, the invention may be used to construct an indwelling blood glucose sensor capable of continuous measurement of glucose levels, although the principle is general and it may be easily seen to extend to the measurement of any analyte of size and charge such that it may be passed through a membrane designed for such purpose.

Example 4

Bioartificial Kidney

Figure 5:
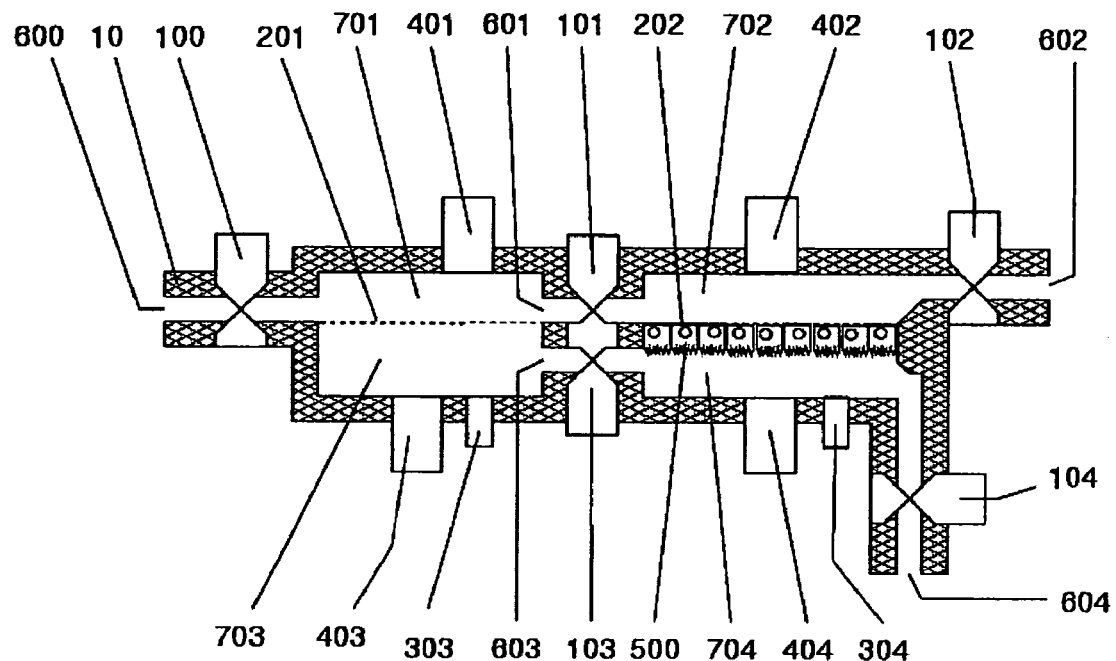
FIG. 5 shows a bioartificial organ in some embodiments of the present invention.

This example demonstrates how nanofabricated nanoporous membranes may be used to form a bioartifical kidney device. A preferred embodiment is shown in FIG. 5. Two membranes 201 and 202 are housed in a housing 10. Blood or other body fluid from a patient is directed via a cannula, vascular graft, vascular anastamosis, or other method into an orifice 600 containing an optional pump or valve 100, which may be peristaltic, rotary, roller, or other, and may be used to regulate a flow of fluid to a chamber in the housing 701, which contains a pressure sensor 401; a membrane 201 composed of a plurality of pores; and an outlet 601 with a flow controlling device such as a pump or valve 101. Said pores may be shaped to optimize hydraulic permeability, and may be all alike or dissimilar. Furthermore, said pores may contain or comprise electrodes, surface treatments, or be coated with chemicals, polymers, proteins, sugars to impart a particular electrostatic charge to the pore or a region around the pore, and impart an electric field within the pore. The outlet 601 and flow controller 101 may be used in conjunction with pressure sensor 401 and pump, valve, or flow controller 100, and external or integrated electronics, telemetry, and information processing to regulate flow of blood or body fluids into and out of chamber 701, and in particular to regulate the hydrostatic pressure in chamber 701. The outlet 601 and flow controller 101 control flow of blood into a second chamber 702, which is equipped with a pressure sensor 402; optionally other sensors incorporating but not limited to optical, conductance, impedance, magnetic resonance, electrochemical, or immunologic principles; and an outlet 602 containing a flow regulating device such as a pump or valve 102. Outlet 602 and its associated flow controller 102 may be used in conjunction with pressure sensor 402 and other pressure sensors and flow controllers and external or integrated electronics, telemetry, and information processing to regulate flow of blood or body fluids into and out of chamber 702, and in particular to regulate the hydrostatic pressure in chamber 702. Blood or body fluids exiting orifice 602 is returned to the patient via a cannula, vascular graft, vascular anastamosis, or other method.

A third chamber 703 is positioned to receive ultrafiltrate generated by hydrostatic pressure or electrosmotic flow of blood or body fluid in chamber 701 passing through the membrane 201, and incorporates a second pressure sensor 403; a sensor or array of sensors 303 incorporating but not limited to optical, conductance, impedance, magnetic resonance, electrochemical, or immunologic principles; and an outlet 603 and flow controller 103. In the example of a bioartificial kidney, it is contemplated that this ultrafiltrate is substantially free of proteins and cellular elements. Flow controller 103 directs ultrafiltrate to a fourth chamber 704, similarly equipped with a pressure sensor 404 and other sensors 304 incorporating but not limited to optical, conductance, impedance, magnetic resonance, electrochemical, or immunologic principles, and an outlet 604 with a flow control mechanism 104. The sensor or array of sensors 304 may be used to monitor the composition of the ultrafiltrate and actuate alarms, valves, or other devices, including but not limited to telemetry and telephony devices, in event that a parameter measured of the ultrafiltrate falls out of a prescribed range.

Chambers 702 and 704 are connected by a second membrane 202 which may be treated, coated, adsorbed, or otherwise modified with cells or tissues. For example, in some embodiments, the cells comprise epithelial, endothelial, fibroblast, or other cells. In some embodiments, the cells are transgenic cells that are engineered to express or not express desired genes (e.g., to modulate the secretion of proteins or other secreted molecules, to express extracellular molecules that bind desired ligands, etc.). In some embodiments, the membrane 202 is also associated with sorbents, enzymes, proteins, channels, porins, or other agents to control and direct the flow of fluids, electrolytes, toxins, peptides, proteins, or other chemicals, through said membrane 202 and into chamber 702 where such fluids, electrolytes, toxins, peptides, proteins, or other chemicals mix with the blood or body fluid that has entered chamber 702 via orifice 601. Blood or body fluid that has been mixed with the cellular and metabolic products of the membrane 202 is then returned to the patient via orifice 602 as described. The ultrafiltrate which has been processed by the second membrane but has not been reabsorbed is carried away from chamber 704 via an outlet 604 and is then carried to a reservoir or to the patient's urinary bladder, an enteric loop, or other suitable disposal route. Through this means, as well as others not specified herein, a patients bloodstream may be filtered and processed to remove solutes, toxins, electrolytes, and water while preserving circulating volume, small peptides, amino acids, and other molecules essential to homeostasis.

A sacrificial oxide technique was used to fabricate arrays of 1 mm×1 mm silicon membranes with 10-100 nm×45 µm slit pores. There were approximately $10^4$ slit pores per array. After etching away the sacrificial oxide, the membranes were epoxied to an acrylic or polycarbonate carrier and inspected via light microscopy for defects. A custom-built apparatus was used to test the membranes. Acrylic was machined to provide two cylindrical half-chambers, each with inlet and outlet Luer fittings. A pressure transducer (Omega PX61) was threaded into a separate port in one chamber. The two halves were bolted together, trapping the membrane and carrier between. Buna-N O-rings provided watertight and gastight seals between the two half-chambers and the membrane carrier. A Luer manifold system allowed regulation of fluid flow into each half chamber. Driving force for gas flow was provided by compressed gas cylinders and for liquid flow by a peristaltic pump. Independent control of flow rate into each chamber and pressure within each chamber was achieved by varying the diameter of tubing draining the chamber. The volumetric flows of gases and liquid were measured by timing positive displacement of a liquid meniscus in calibrated pipettes or syringes.

Nitrogen and carbon dioxide were individually used to flush both sides of the membranes. The outlet of the feed side and the inlet of the permeate side were closed. The outlet on the permeate side was connected to the top of a pipette filled with vacuum oil. The feed side was pressurised at 1.00, 1.25, 1.50, 1.75, and 2.00 psi, and the downward displacement of oil was timed at each pressure. By regulating the height of the meniscus from run to run, the outlet pressure was held to within 2-3 cm oil from experiment to experiment. Tests with dummy membranes without pores and open membranes with macroscopic holes were also conducted to validate the system. The gas flow through the membranes was used initially to confirm that the membrane pores were open and were consistent in performance between and within wafers. Furthermore, carbon dioxide is an ideal wetting agent prior to aqueous experiments, as $CO_2$ bubbles readily dissolve into aqueous solution and allow avoidance of surface tension issues with nitrogen bubbles. Phosphate buffered saline (PBS) was stored in a reservoir and circulated with a peristaltic pump. After membrane flushing with carbon dioxide to exclude air bubbles within the pores, both sides of the membranes were flushed with PBS, and the inlet port of the permeate side sealed. The outlet port was connected to a calibrated syringe barrel, and an oil seal was placed on the syringe barrel. Flow through the feed side of the chamber was adjusted to produce transmembrane pressures of 1.00, 1.25, 1.50, 1.75 and 2.00 psi. Volumetric displacement of the PBS-air meniscus under the oil seal was timed to calculate volume flow. Pressure-flow curves were generated for each pore size and hydraulic permeabilities for PBS were calculated. Measured hydraulic permeabilities correlated well with Navier-Stokes predictions for Hele-Shaw flows (Fissell et al., J. Amer. Soc. Nephrology, vol. 13, pp. 602A, 2002). Also noteworthy were the similarities in hydraulic permeabilities (Kuf) of the silicon nanoporous membranes and commercial polymer dialysis membranes (Fresenius and Baxter). This is particularly interesting considering that the silicon membranes have a porosity that is orders of magnitude smaller than that of polymer membranes.

Silicon chips 1×1 cm square were diced from a 100 mm diameter, 500 μm thick, <100>-oriented n-type single-side polished wafer. Similarly, 1×1 cm square chips of polycrystalline silicon (polysilicon) were diced from a 100 mm diameter, <100>-oriented, n-type single side polished wafer that was oxidized to grow a 1000 Å-thick oxide layer followed by the deposition of a 5 μm thick polysilicon film by low-pressure chemical vapor deposition. Murine collagen IV and fetal calf serum were nonspecifically adsorbed onto steam-autoclaved silicon and polysilicon chips, which were placed in 12 mm-diameter tissue culture wells. Human renal proximal tubule cells (RPTCs) were harvested from transplant discards and grown to fourth passage on 100 mm-diameter tissue culture plates, resuspended, and stained with a fluorescent cell linker (PKH26-GL, Sigma, St. Louis) (Humes et al., Amer. J. Physiology, 271:F42, 1996). Aliquots of $10^5$ cells were layered onto silicon and polysilicon chips with preadsorbed extracellular matrix proteins.

Cell growth was monitored by light microscopy in control wells. When cells reached approximately 75% confluence, 90% confluence, and complete confluence, chips were removed from tissue culture media and fixed in cold 4% paraformaldehyde for 20 minutes and then rinsed with cold phosphate buffered saline and stored in PBS at 0° C. Renal proximal tubule cells were observed to attach to single-crystal silicon and polysilicon chips when pretreated with ECM proteins, and retain surface markers characteristic of renal proximal tubule cells, including tight junction proteins. Specifically, areas of the silicon chips where the membranes were open and porous (M) were compared with areas where the silicon surface was identically textured and prepared, but a monocrystalline silicon backing layer occluded the pores (S). Silicon chips bearing membranes upon which HPTCs had been grown to confluence were incubated with antibodies to two protein markers of differentiation (acetylated tubulin (AT1) and ZO-1). Fluorescently labeled secondary antibodies were then used to examine the cells by immunofluorescence microscopy. A fluorescent marker for cell nuclei (DAPI) was used as a control. Cells attached to S areas and M areas in approximately equal density, and intensity of fluorescence of the DAPI stain did not vary appreciably between S areas and M areas. ZO-1 expression on the surfaces of HPTCs in M areas was increased compared with S areas, although at the time of cell fixation it had not localized to intercellular junctions. Intensity of fluorescence of DAPI was similar between the two areas. Acetylated tubulin is a component of the primary cilium of renal proximal tubule cells. Acetylated tubulin staining in M areas was more intense than in S areas, although DAPI staining remained uniform in intensity over the two areas. These observations show that detailed structuring of surface textures and porosity of silicon nanomembranes has direct impact of cellular differentiation.

Example 5

Nanoporous Membranes for Bioartifical Organs

Figure 6:
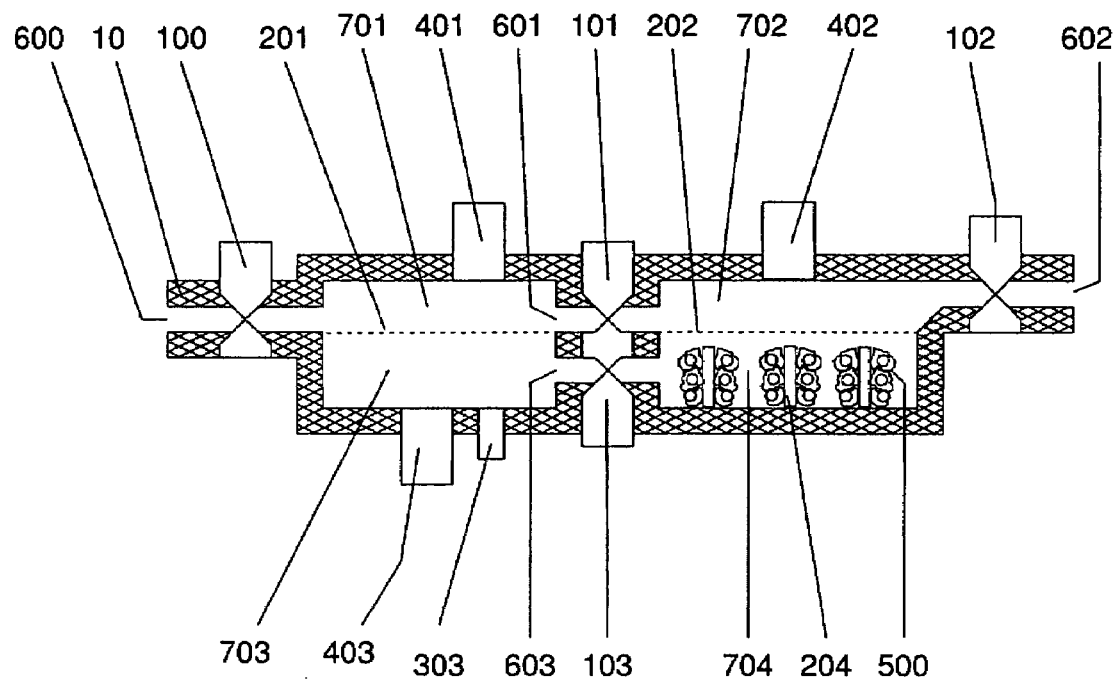
FIG. 6 shows a bioartificial organ in some embodiments of the present invention.

This example demonstrates how nanofabricated nanoporous membranes may be used to form a bioartifical kidney device. A preferred embodiment is shown in FIG. 6. Two membranes 201 and 202 are housed in a housing 10. Blood or other body fluid from a patient is directed via a cannula, vascular graft, vascular anastamosis, or other method into an orifice 600 containing an optional pump or valve 100, which may be peristaltic, rotary, roller, or other, and may be used to regulate a flow of fluid to a chamber in the housing 701, which contains a pressure sensor 401; a membrane 201 composed of a plurality of pores; and an outlet 601 with a flow controlling device such as a pump or valve 101. Said pores may be shaped to optimize hydraulic permeability, and may be all alike or dissimilar. Furthermore, said pores may contain or comprise electrodes, surface treatments, or be coated with chemicals, polymers, proteins, sugars to impart a particular electrostatic charge to the pore or a region around the pore, and impart an electric field within the pore. The outlet 601 and flow controller 101 may be used in conjunction with pressure sensor 401 and pump, valve, or flow controller 100, and external or integrated electronics, telemetry, and information processing to regulate flow of blood or body fluids into and out of chamber 701, and in particular to regulate the hydrostatic pressure in chamber 701. The outlet 601 and flow controller 101 control flow of blood into a second chamber 702, which is equipped with a pressure sensor 402; optionally other sensors incorporating but not limited to optical, conductance, impedance, magnetic resonance, electrochemical, or immunologic principles; and an outlet 602 containing a flow regulating device such as a pump or valve 102. Outlet 602 and its associated flow controller 102 may be used in conjunction with pressure sensor 402 and other pressure sensors and flow controllers and external or integrated electronics, telemetry, and information processing to regulate flow of blood or body fluids into and out of chamber 702, and in particular to regulate the hydrostatic pressure in chamber 702. Blood or body fluids exiting orifice 602 is returned to the patient via a cannula, vascular graft, vascular anastamosis, or other method.

A third chamber 703 is positioned to receive ultrafiltrate generated by hydrostatic pressure or electrosmotic flow of blood or body fluid in chamber 701 passing through the membrane 201, and incorporates a second pressure sensor 403; a sensor or array of sensors 303 incorporating but not limited to optical, conductance, impedance, magnetic resonance, electrochemical, or immunologic principles; and an outlet 603 and flow controller 103. In the example of a bio-artificial kidney, it is contemplated that this ultrafiltrate is substantially free of proteins and cellular elements. Flow controller 103 directs ultrafiltrate to a fourth chamber 704, optionally equipped with a pressure sensor and other sensors not shown incorporating but not limited to optical, conductance, impedance, magnetic resonance, electrochemical, or immunologic principles. In some embodiments, chamber 704 is fitted with nanofabricated or other assemblies 204, which may be treated, coated, adsorbed, or otherwise modified with cells or tissues 500. In some embodiments, these cells may be pancreatic islet cells. In some embodiments these may be hepatocytes. In other embodiments these may be transgenically modified cells, prokaryotic or eukaryotic cells, bone marrow cells, xenotransplanted cells, allografted cells, or stem cells of embryonic or adult origin of human or other species. These examples shall not be construed as limiting the type, variety and mixtures of cells to be employed. In this example, cells 500 are permitted to be bathed by the ultrafiltrate of blood generated by membrane 201 and delivered to them from chamber 703 via orifice 603. In some embodiments, said ultrafiltrate is free of immunoglobulins, complement components of blood, chemotherapeutic agents, or other entities in the blood harmful to cells 500. Said cells 500 may metabolize toxins in the ultrafiltrate, in the example in which they are hepatocytes, or may sense the concentration of some entity in the ultrafiltrate, such as glucose, and respond by secreting a hormone or other molecule, such as insulin. In another embodiment, cells 500 may be renal cells that secrete erythropoetin in response to oxygen tension in the ultrafiltrate. Chambers 702 and 704 are connected by a second membrane 202 that may be treated, coated, adsorbed, or otherwise modified with cells or tissues. In some embodiments, the membrane 202 is also associated with sorbents, enzymes, proteins, channels, porins, or other agents to control and direct the flow of fluids, electrolytes, toxins, peptides, proteins, or other chemicals, through said membrane 202 and into chamber 702 where such fluids, electrolytes, toxins, peptides, proteins, or other chemicals mix with the blood or body fluid that has entered chamber 702 via orifice 601. In some embodiments, the porous structure of membrane 202 is designed to prevent passage of a specified protein, peptide, sugar, lipid, bacterium, or other entity into chamber 702. Blood or body fluid that has been mixed with the cellular and metabolic products of the membrane 202 is then returned to the patient via orifice 602 as described. Through this means, as well as others not specified herein, a patient may receive a dose of cells of arbitrary type while such cells are protected from the immune effectors in the blood, while receiving convective transport of nutrients and oxygen from the blood, and the biological products of such cells may re-enter the patient's bloodstream in a controlled fashion.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claimed:

1. An ultrafiltration system comprising:
   a) a membrane comprising micromachined pores having a length and a width, said length being less than 200 microns and said width being less than 200 nanometers, wherein the ratio of said length to said width is at least 5:1;
   b) a housing containing said membrane, wherein said housing comprises a coating, said coating being biocompatible for in vivo use; and
   c) a fluid delivery passageway with a first end and a second end, said first end positioned outside of said housing, said second end positioned to delivery fluid across said membrane.

2. The system of claim 1, wherein said length is less than 100 microns.

3. The system of claim 1, wherein said width is less than 100 nanometer.

4. The system of claim 1, wherein said ratio is at least 10:1.

5. The system of claim 1, wherein said system further comprises one or more electrodes positioned on or near said membrane such that an electric field is generated in or near said pores.

6. The system of claim 1, wherein said housing has a length and a width, said length of said housing being less than 300 millimeters and said width of said housing being less than 300 millimeters.

7. A method of filtering a biological fluid comprising:
   a) providing an ultrafiltration system comprising
      i) a membrane comprising micromachined pores having a length and a width, said length being less than 200 microns and said width being less than 200 nanometers, wherein the ratio of said length to said width is at least 5:1;
      ii) a housing containing said membrane; and
      iii) a fluid delivery passageway with a first end and a second end, said first end positioned outside of said housing, said second end positioned to delivery fluid across said membrane;
   b) connecting said system to a subject's vasculture; and
   c) passing biological fluid from said vasculature through said system to generate filtered biological fluid.

8. The method of claim 7, wherein said connecting comprises placing said system into a subject.

9. The method of claim 7, wherein said filtered fluid is substantially free of proteins.

10. The method of claim 7, wherein an electric field is produced under conditions such that said pores provide a charge and size selective barrier to proteins.

11. The method of claim 10, wherein said electric field is produced under conditions such that protein fouling is reduced in said pores.

12. The method of claim 7, wherein said filtered fluid comprises hemofiltered fluid.

13. A method of filtering a biological fluid comprising:
   a) providing a bioartificial ultrafiltration device comprising:
      i) a housing;
      ii) an inlet port passing through said housing, said inlet port configured to receive a biological fluid;
      iii) an outlet port passing through said housing, said outlet port configured to return a biological fluid to a subject;
      iv) a membrane contained in said housing, said membrane comprising micromachined pores; and
      v) a population of cells attached to said membrane;
   b) connecting said system to a subject's vasculture; and
   c) passing biological fluid from said vasculature through said device to generate filtered biological fluid.

14. The method of claim 13, wherein said connecting comprises placing said system into a subject.

15. The method of claim 13, wherein said filtered fluid is substantially free of proteins.

16. The method of claim 13, wherein an electric field is produced under conditions such that said pores provide a charge and size selective barrier to proteins.

17. The method of claim 16, wherein said electric field is produced under conditions such that protein fouling is reduced in said pores.

18. The method of claim 13, wherein said filtered fluid comprises hemofiltered fluid.

19. The method of claim 13, wherein said pores have a length and a width, said length being less than 200 microns and said width being less than 200 nanometers, wherein the ratio of said length to said width is at least 5:1.

20. The method of claim 13, wherein said device further comprises one or more electrodes positioned on or near said membrane such that an electric field is generated in or near said pores.

21. The method of claim 13, wherein said cells are selected from the group consisting of renal tubule cells, pancreatic cells, hepatic cells, thyroid cells, adrenal cells, parathyroid cells, pituitary cells, hypothalamic cells, gonadal cells, prokaryotic cells, duodenal cells, gastric cells, intestinal cells, muscle cells, fibroblast cells, and endothelial cells.

* * * * *